(12) United States Patent
Hayashizaki et al.

(10) Patent No.: US 6,383,356 B1
(45) Date of Patent: May 7, 2002

(54) CAPILLARY ELECTROPHORETIC APPARATUS

(75) Inventors: Yoshihide Hayashizaki, Ibaraki; Shin Nakamura, Kyoto, both of (JP)

(73) Assignee: Japan Science and Technology Corporation, Kawaguchi (JP)

( * ) Notice: Subject to any disclaimer, the term of this patent is extended or adjusted under 35 U.S.C. 154(b) by 0 days.

(21) Appl. No.: 09/448,139

(22) Filed: Nov. 24, 1999

(30) Foreign Application Priority Data

Nov. 30, 1998 (JP) ............................... 10-338898

(51) Int. Cl.[7] ............................... G02N 27/26
(52) U.S. Cl. ................ 204/605; 204/601; 204/455
(58) Field of Search ................ 204/600, 601, 204/455, 451, 605

(56) References Cited

U.S. PATENT DOCUMENTS 5,332,481 A * 7/1994 Guttman ............... 204/455
5,635,050 A * 6/1997 Pentoney, Jr. et al. ...... 204/605

* cited by examiner

Primary Examiner—Lyle A. Alexander
Assistant Examiner—Alex Noguerola

(57) ABSTRACT

A drain joint of a pump block is opened, a piston (19a) is pushed while a piston (13a) is fixed, for charging a passage between a Luer-Lok joint (17) and an intersection part as well as a passage between the intersection part and the drain joint with a buffer. Thereafter the piston (13a) is pushed while the piston (19a) is fixed, to charge a passage (7a) with a polymer. Then, the drain joint is closed, the piston (13a) is pushed and the piston (19a) is pulled in response to the amount of pushing, for charging the passage between the intersection point and the Luer-Lok joint (17) with the polymer. Thereafter, the piston (13a) is pushed while the piston (19a) is fixed, to charge a capillary column with the polymer.

6 Claims, 4 Drawing Sheets

CAPILLARY ELECTROPHORETIC APPARATUS

BACKGROUND OF THE INVENTION

1. Field of the Invention

The present invention relates to a gel electrophoretic apparatus for separating and analyzing a biopolymer such as protein or nucleic acid, and more particularly, it relates to a capillary electrophoretic apparatus employing a capillary tube.

Such a capillary electrophoretic apparatus is employed in the biochemical field and for clinical testing, in particular as a DNA sequencer to obtain excellent results.

2. Description of the Prior Art

A DNA sequencer having high sensitivity, high speed and high throughput is necessary for sequence determination for DNA such as a human genome having long base sequence. For example, capillary electrophoresis employing a capillary column charged with a polymer serving as a separation medium is performed in place of slab gel electrophoresis employing a flat plate type slab gel. The separation medium is formed by a polymer and may be referred to as a polymer. With such a capillary column, a sample can not only be readily handled or injected, but also electrophoresed at a high speed to be detected in high sensitivity as compared to the slab gel. If a high voltage is applied to the slab gel, a band is spread or a temperature gradient is caused due to influence by Joulean heat. However, the capillary column hardly causes such a problem but can perform detection in high sensitivity with small band spreading even if performing high-speed electrophoresis with application of a high voltage.

A multi-capillary DNA sequencer prepared by arranging a plurality of capillary columns is also proposed.

In the capillary electrophoresis, a capillary column is charged with a polymer in the exterior of a capillary electrophoretic apparatus and thereafter mounted on the capillary electrophoretic apparatus. The capillary column and the polymer once used are discarded after electrophoresis and analysis. Thus, the running cost is increased, and the capillary column charged with a polymer having low viscosity is difficult to operate.

In order to reduce a cost and simplify handling of a capillary column charged with a polymer, there are proposed the following apparatuses: an apparatus (prior art 1) employing a polymer based on a cross-liking gel, and comprising a mechanism for reuse the polymer, a capillary column reuse type apparatus (prior art 2) comprising a mechanism charging and exchanging a polymer through a gas pressure, and a capillary column reuse type apparatus (prior art 3) comprising a syringe charge type mechanism for switching a valve mechanism and bringing a polymer into contact with a buffer solution, and the like.

In the prior art 1, it is difficult to charge the capillary column with the cross-linking gel with high yield since the inner part of the capillary column must be coated and bubbles may be mixed when reusing the cross-linking gel.

The prior art 2 requiring high-pressure gas of about 70 kgf/cm² is difficult to operate. In particular, a multi-capillary lectrophoretic apparatus simultaneously handling a plurality of capillary columns requires a higher pressure and is more difficult to operate.

In the prior art 3, the polymer may leak from the valve mechanism when charged by a syringe with a high liquid pressure, to reduce the yield. In a multi-capillary electrophoretic apparatus, the mechanism is disadvantageously complicated.

SUMMARY OF THE INVENTION

Accordingly, an object of the present invention is to provide a capillary electrophoretic apparatus comprising a polymer charging mechanism capable of readily charging a capillary column with a polymer in a high yield.

The capillary electrophoretic apparatus according to the present invention comprises a capillary electrophoretic part electrophoresing a sample injected into a capillary column charged with a polymer, a detection part detecting each component separated in the capillary column on an appropriate position of the capillary column, a polymer syringe charged with a polymer, a pump block connecting the polymer syringe with one end of the capillary column through a passage, and a high voltage power supply device having electrodes provided on the one end and the other end of the capillary column so that the electrode provided on the one end comes into contact with the polymer for applying an electrophoresis voltage between the both ends of the capillary column with the electrodes.

In one aspect of the present invention, the pump block comprises a polymer port connected with the polymer syringe, a column port connected with the one end of the capillary column and a passage connecting the polymer port and the column port with each other, and the electrode on the one end of the capillary column is provided to come into contact with the polymer in the polymer syringe or the pump block.

In the capillary electrophoretic apparatus according to this aspect, the one end of the capillary column and the polymer syringe are connected to the pump block, and a piston of the polymer syringe is thereafter pushed to charge the capillary column with the polymer charged in the syringe through the passage of the pump block. Thereafter, a voltage is applied between both ends of the capillary column through the electrodes provided on both ends of the capillary column while connecting the capillary column with the pump block.

In another aspect of the present invention, the capillary electrophoretic apparatus further comprises a buffer syringe charged with a buffer, the pump block comprises a polymer port connected with the polymer syringe, a buffer port connected with the buffer syringe, a column port connected with the one end of the capillary column and a passage connecting the ports with each other, and the electrode on the one end of the capillary column is provided to come into contact with the polymer through the buffer.

It is preferable to form an openable drain port on the pump block and connect this drain port to the passage of the pump block.

In the capillary electrophoretic apparatus according to this aspect, after the drain port is opened, a piston of the buffer syringe is pushed while a piston of the polymer syringe is fixed, thereby air in the passage between the buffer syringe and the drain port is discharged through the drain port and the passage is charged with the buffer. Then, the piston of the buffer syringe is fixed and the piston of the polymer syringe is pushed while the drain port is kept open, thereby the buffer in the passage between the polymer syringe and the drain port is discharged through the drain port, and the passage is charged with the polymer. After the drain port is sealed, the piston of the polymer syringe is pushed and the piston of the buffer syringe is pulled in response to the amount of pushing, thereby the passage between the polymer syringe and the buffer syringe is charged with the polymer. Thereafter, the piston of the polymer syringe is pushed while the buffer syringe is fixed, thereby the passage between the polymer syringe and the capillary column as well as the capillary column are charged with the polymer.

It is preferable to comprise a pressure sensor measuring the pressure in the passage of the pump block. It is possible to charge the polymer, while monitoring the pressure in the passage with the pressure sensor for previously detecting abnormality such as clogging of the capillary column from the pressure value.

It is preferable to further comprise a tray storing a sample, a buffer and purified water, and a tray driving mechanism moving the tray for inserting the other end of the capillary column and the electrode into the sample, the buffer or the purified water. Consequently, sample injection, and separation and analysis after polymer charging can be automated by controlling the applied voltage and operations of the tray driving mechanism.

Thus, according to the present invention, the polymer syringe and the capillary column are connected by the passage in the pump block, and the syringe is pushed to charge the capillary column with the polymer, whereby the capillary column can be readily charged with the polymer in a high yield.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
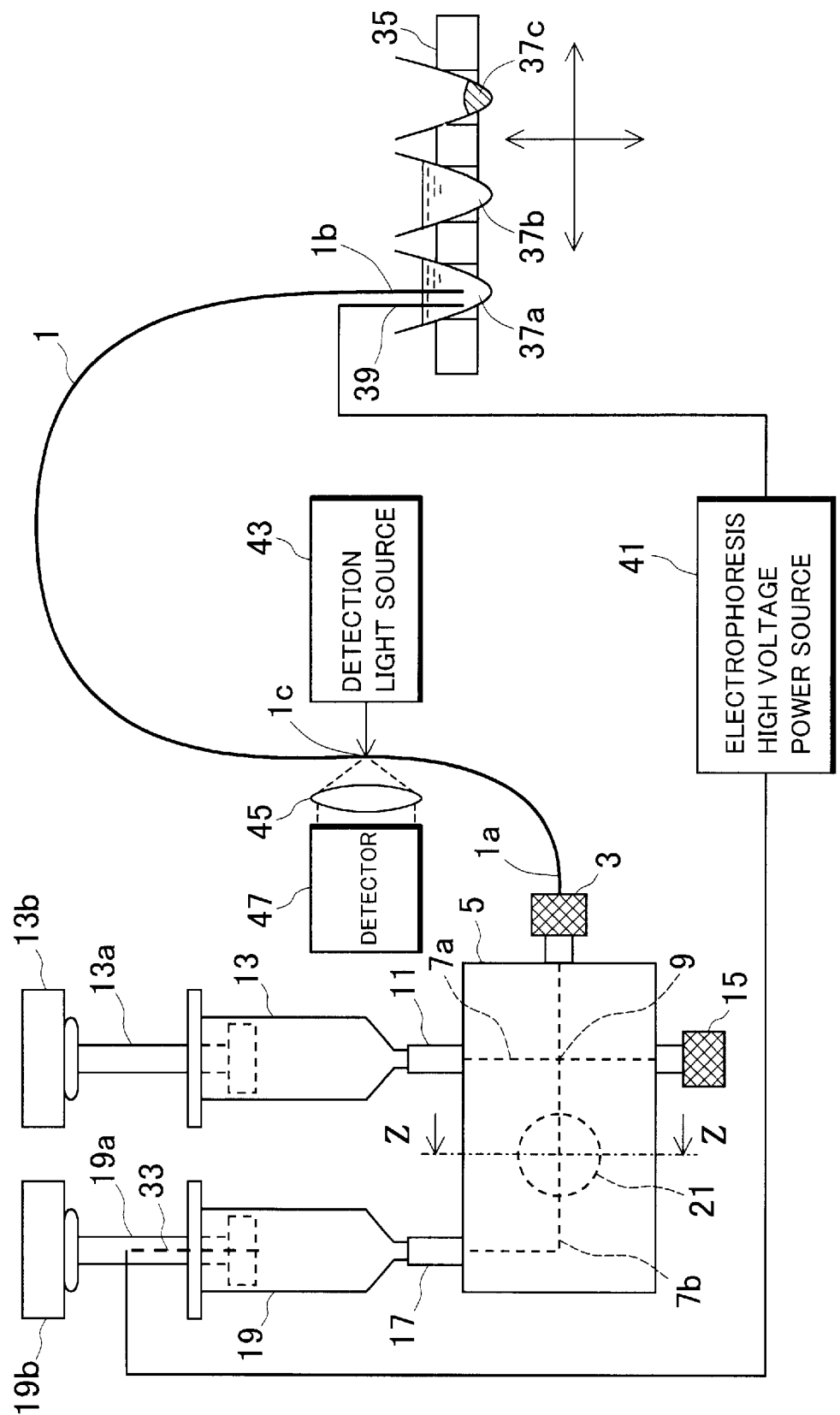
FIG. 1 is a schematic front elevation view showing an embodiment of the present invention.

FIG. 1 is a schematic front elevation view showing a capillary electrophoretic apparatus according to an embodiment of the present invention.

Numeral 1 denotes a capillary column having an outer diameter of 200 to 300 μm and an inner diameter of 50 to 150 μm, which is made of fused silica. One end 1a of the capillary column 1 is connected to a pump block 5 through a capillary joint 3. The pump block 5 is provided therein with two passages 7a and 7b of 1 to 3 mm in diameter, which are connected with each other at an intersection part 9.

A polymer syringe 13 charged with a polymer is connected to one end of the passage 7a through a Luer-Lok joint 11. The other end of the passage 7a is sealed with a switchable drain joint 15.

Figure 2:
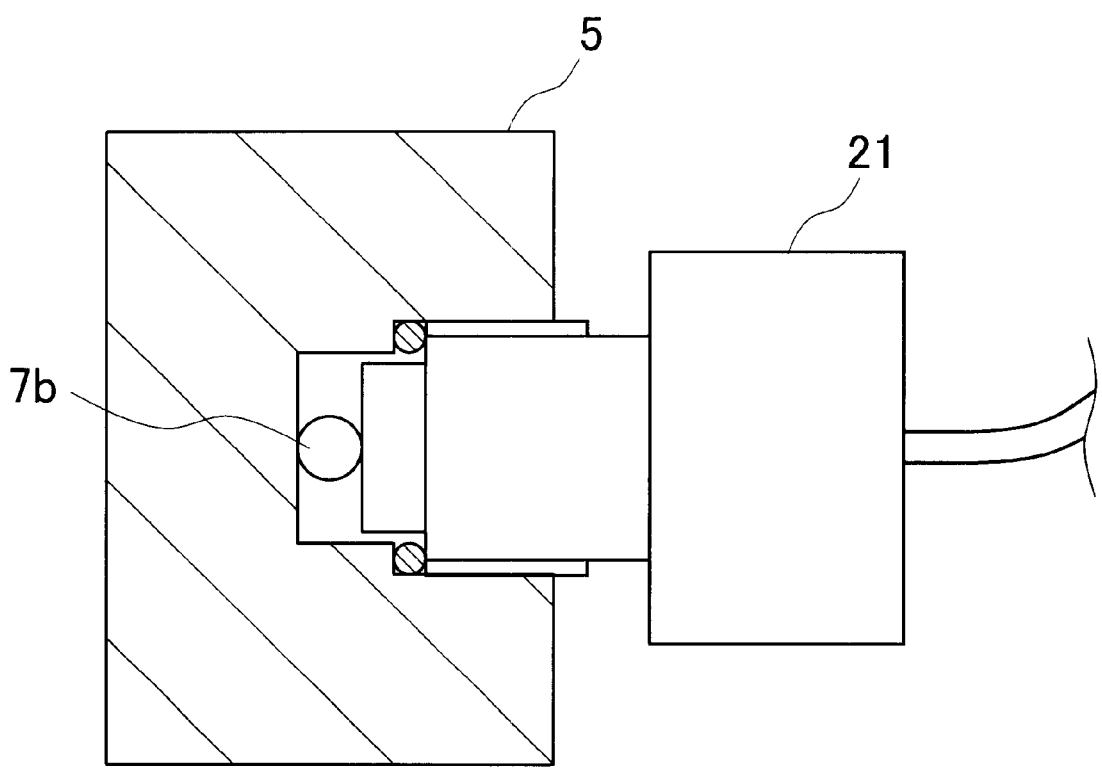
FIG. 2 is a sectional view showing a pressure sensor of the embodiment.

A buffer syringe 19 charged with a buffer is connected to one end of the passage 7b through a Luer-Lok joint 17. The capillary column 1 is connected to the other end of the passage 7b through the capillary joint 3. As shown in FIG. 2, a pressure sensor 21 measuring the pressure in the passage 7b is provided on the passage 7b between the intersection part 9 and the Luer-Lok joint 17. FIG. 2 is a sectional view taken along the line Z—Z in FIG. 1.

An electrode 33 consisting of a platinum wire is embedded in a piston 19a of the buffer syringe 19 so that its forward end is in contact with the buffer in the buffer syringe 19.

Syringe piston driving linear actuators 13b and 19b drive a piston 13a of the polymer syringe 13 and the piston 19a of the buffer syringe 19 respectively.

Figure 3:
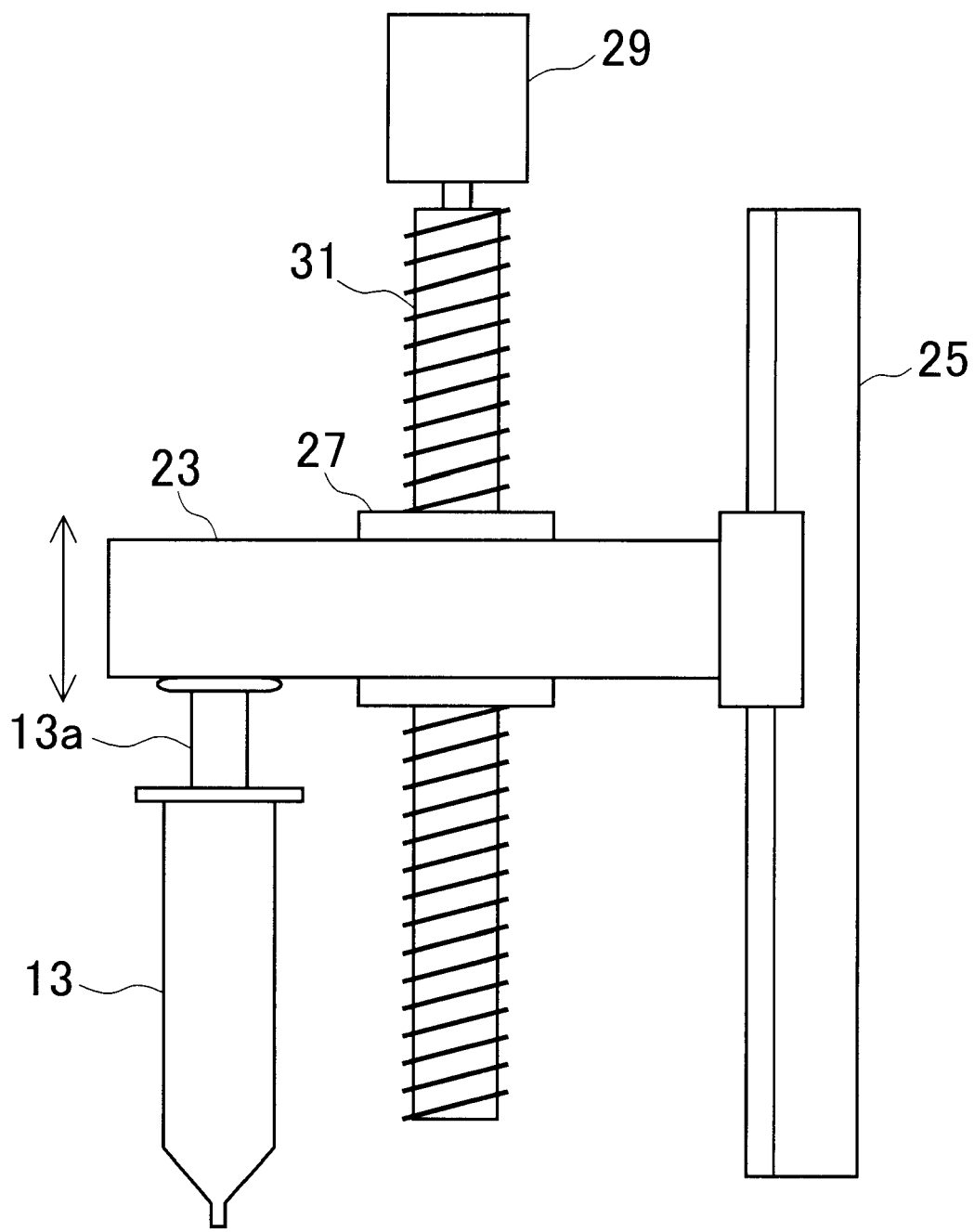
FIG. 3 is a schematic front elevation view showing an exemplary syringe piston driving linear actuator of the embodiment.

FIG. 3 is a front elevation view showing an example of the syringe piston driving linear actuator 13b for the polymer syringe 13. The syringe piston driving linear actuator 19b for the buffer syringe 19 is identical in structure to the syringe piston driving linear actuator 13b.

One end of a coupling member 23 is fixed to the piston 13a, and the other end thereof is slidably supported on a guide 25 set in parallel with the sliding direction of the piston 13a. A female screw 27 engaging with a rod screw 31 driven by a stepping motor 29 is fixed to the coupling member 23. The stepping motor 29 rotates the rod screw 31, so that the coupling member 23 slides along the guide 25 and the piston 13a also slides.

Referring again to FIG. 1, the other end 1b of the capillary column 1 is dipped in purified water 37a stored in a container set on a tray 35 with an electrode 39 consisting of a platinum wire. Other containers on the tray 35 store a buffer 37b and a sample 37c respectively. The tray 35 is vertically and horizontally movable along arrows by a tray driving mechanism (not shown), so that the other end 1b of the capillary column 1 is dipped in the purified water 37a, the buffer 37b or the sample 37c as needed.

The electrodes 33 and 39 are connected to an electrophoresis high voltage power source 41 for serving as an anode and a cathode respectively and applying a high voltage to the both ends 1a and 1b of the capillary column 1 in sample introduction and electrophoresis.

A detection light source 43 such as an Ar laser unit applying light to a part to be detected 1c of the capillary column 1 and a detector 47 detecting light from the part 1c through a condensing and spectroscopic part 45 are arranged in the vicinity of the part 1c as a detection part.

Operations for charging the capillary column 1 with a polymer shall now be described.

The Luer-Lok joint 11 connects the polymer syringe 13 charged with the polymer to the passage 7a of the pump block 5, and the piston 13a is fixed to the syringe piston driving linear actuator 13b. The Luer-Lok joint 17 connects the buffer syringe 19 charged with the buffer to the passage 7b of the pump block 5, and the piston 19a is fixed to the syringe piston driving linear actuator 19b. The containers storing the purified water 37a, the buffer 37b and the sample 37c are arranged on the tray 35 respectively. The capillary joint 3 connects the one end 1a of the capillary column 1 to the passage 7b of the pump block 5 for mounting the capillary column 1. The tray 35 is moved to dip the other end 1b of the capillary column 1 and the electrode 39 into the purified water 37a.

After the drain joint 15 is opened, the piston 19a is pushed while the piston 13a is fixed, thereby the passage 7b between the Luer-Lok joint 17 and the intersection part 9 and the passage 7a between the intersection part 9 and the drain joint 15 are charged with the buffer. Then, the piston 13a is pushed while the piston 19a is fixed, thereby the passage 7a is charged with the polymer and the buffer charged in the passage 7a between the intersection part 9 and the drain joint 15 is discharged through the drain joint 15.

When the passages 7a and 7b are charged with the polymer and the buffer, the capillary joint 3 is opened through the capillary column 1 while the inner diameter of the capillary column 1 is small and hence passage resistance is developed to guide the polymer and the buffer only to the drain joint 15.

After the drain joint 15 is closed, the syringe piston driving linear actuators 13b and 19b are synchronously driven at the same speed for pushing the piston 13a, pulling the piston 19a, and charging the passage 7b between the intersection part 9 and the Luer-Lok joint 17 with the polymer.

Then, the piston 19a is fixed and the piston 13a is pushed for charging the capillary column 1 with the polymer through the intersection part 9 and the capillary joint 3. At this time, the pressure sensor 21 monitors the pressure in the passage 7b, so that various problems such as clogging of the capillary column 1 can be detected in an early stage.

After charging the polymer, the tray 35 is moved to dip the other end 1b of the capillary column 1 and the electrode 39 into the sample 37c. The electrophoresis high voltage power source 41 applies a prescribed voltage, for injecting the sample 37c into the capillary column 1.

Thereafter, the tray 35 is moved to dip the other end 1b of the capillary column 1 and the electrode 39 into the buffer 37b. The electrophoresis high voltage power source 41 applies a prescribed voltage for electrophoresing and separating the sample 37c in the capillary column 1. Separated components successively pass through the part to be detected 1c, so that the detector 47 detects interaction with the sample 37c caused by light from the detection light source 43 through the condensing and spectroscopic part 45.

After completing detection of the sample 37c, the tray 35 is moved to dip the other end 1b of the capillary column 1 and the electrode 39 into the purified water 37a, and thereafter the piston 13a is pushed for discharging the polymer from the capillary column 1 through the other end 1b thereof, and charging the capillary column 1 with a new polymer thereby preparing for analysis of a next sample.

After charging the capillary column 1 with the polymer initially, it is preferable to make control to automatically exchange the polymer.

While the passage 7b between the intersection part 9 in the pump block 5 and the Luer-Lokjoint 17 is charged with the buffer before the same is charged with the polymer in this embodiment, the buffer charging operation may be omitted, and the passage 7b between the intersection part 9 and the Luer-Lok joint 17 may be charged with the polymer after charging the passage 7a with the polymer. In this case, air present in the passage 7b between the intersection part 9 and the Luer-Lok joint 17 is fed into the buffer syringe 19. Therefore, it is preferable to project the forward end of the electrode 33 from the forward end of the piston 19a to some extent so that the electrode 33 comes into contact with the buffer also when the air is fed into the syringe 19.

Alternatively, the passage 7b between the intersection part 9 and the Luer-Lok joint 17 may be previously charged with the polymer so that no air enters the buffer syringe 19.

While the electrode 33 is embedded in the piston 19a in this embodiment, the part connecting for example the buffer syringe 19 with the Luer-Lok joint 17 may be formed by an electrode, so far as the electrode comes into contact with the buffer.

Furthermore, the pressure sensor 21 may be omitted and an encoder or the like may be provided on the syringe piston driving linear actuator 13b for monitoring motion of the syringe piston driving linear actuator 13b or loss of synchronism of the stepping motor 29 thereby monitoring various problems such as clogging of the capillary column 1 during polymer charging.

Figure 4:
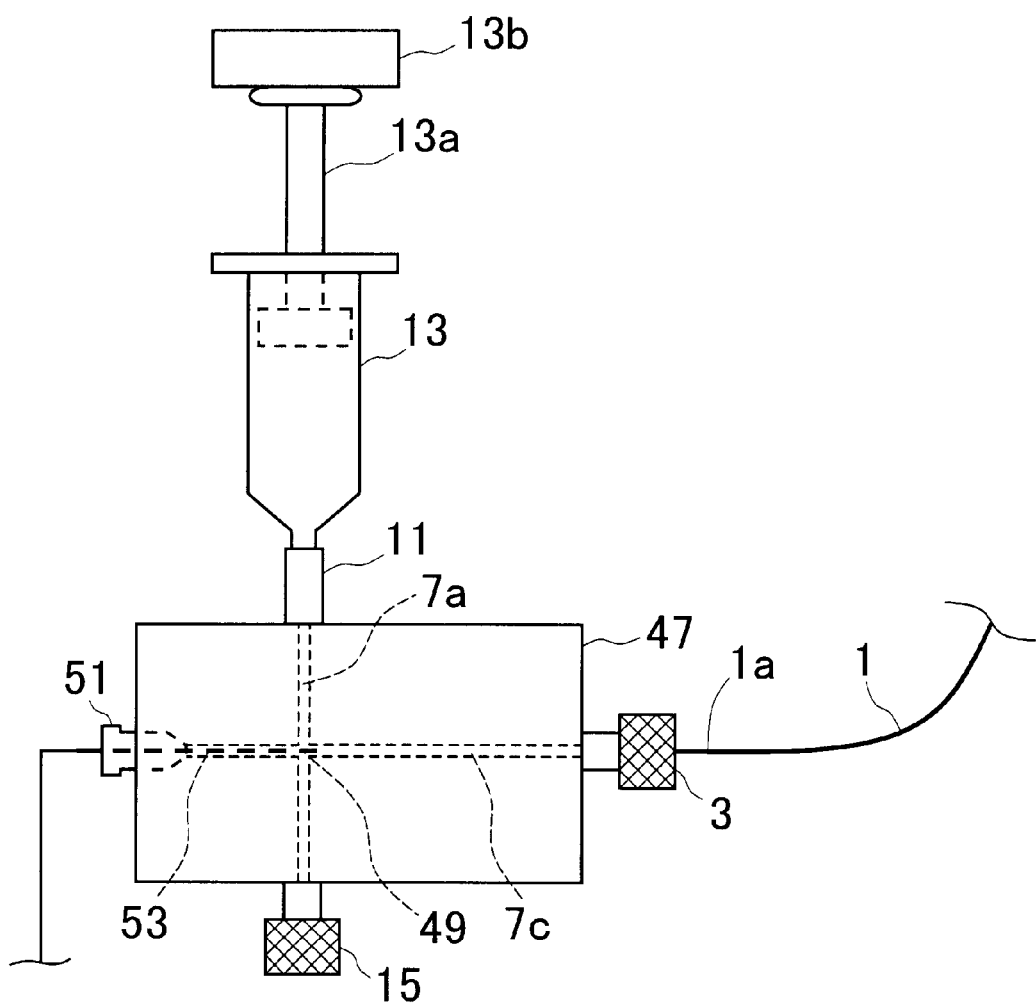
FIG. 4 is a schematic front elevation view showing another embodiment of the present invention.

FIG. 4 is a schematic elevation view showing a structure around a pump block 47 in another embodiment of the present invention.

One end 1a of a capillary column 1 is connected to one end of a passage 7c of the pump block 47 through a capillary joint 3. The pump block 47 is provided therein with two passages 7a and 7c of 1 to 3 mm in diameter, which are connected with each other at an intersection part 49.

A polymer syringe 13 is connected to one end of the passage 7a through a Luer-Lok joint 11 while the other end thereof is sealed with a drain joint 15.

A ferrule 51 is provided on the other end of the passage 7c, and an electrode 53 reaching the intersection part 49 from the ferrule 51 is inserted in the passage 7c. The ferrule 51 airtightly fixes the electrode 53.

Operations of charging the capillary column 1 with a polymer in the embodiment shown in FIG. 4 shall now be described.

The polymer syringe 13 charged with the polymer is connected to the Luer-Lok joint 11 and a piston 13a is fixed to a syringe piston driving linear actuator 13b. The one end 1a of the capillary column 1 is connected to the capillary joint 3 and the other end thereof is dipped into purified water.

After the drain joint 15 is opened, the piston 13a is pushed for charging the passage 7a with the polymer. At this time, the capillary joint 3 is opened through the capillary column 1 while the inner diameter of the capillary column 1 is small and hence passage resistance is developed to guide the polymer only to the drain joint 15.

After the drain joint 15 is closed, the syringe piston driving linear actuator 13b is driven to push the piston 13a for charging the capillary column 1 with the polymer through the intersection part 49 and the capillary joint 3. The polymer comes into contact with the electrode 53 in the passage 7c.

Then, after a sample is separated and analyzed similarly to the embodiment shown in FIG. 1, the syringe piston driving linear actuator 13b is driven to push the piston 13a for exchanging the polymer in the capillary column 1 with a new polymer.

The inventive capillary electrophoretic apparatus is of a capillary reuse type exchanging a polymer every analysis, whereby the running cost can be reduced. Furthermore, the apparatus using no high pressure gas is easy to handle. In addition, no complicated valve mechanism is provided and hence there is no apprehension of leakage of the polymer and the buffer.

While each of the embodiments shown in FIGS. 1 and 4 is applied to a capillary electrophoretic apparatus employing a single capillary column, the present invention is also applicable to a multi-capillary electrophoretic apparatus. When the present invention is applied to a multi-capillary electrophoretic apparatus, the passage in the pump block connected with the capillary column may be branched for providing capillary joints on branched parts of the passage respectively and fixing ends of a plurality of capillary columns to the pump block. Alternatively, ends of a plurality of capillary columns may be collectively inserted in and airtightly fixed to the capillary joint. Thereby, the polymer can be simultaneously injected into the plurality of capillary columns.

Although the present invention has been described and illustrated in detail, it is clearly understood that the same is by way of illustration and example only and is not to be taken by way of limitation as the spirit and scope of the present invention are limited only by the terms of the appended claims.

What is claimed is:

1. A capillary electrophoretic apparatus comprising:
   a capillary electrophoretic part configured to perform electrophoresis of a sample injected into a capillary column charged with a polymer;
   a detection part detecting each component separated in the capillary column on an appropriate position of the capillary column;
   a polymer syringe charged with a polymer;
   a pump block connecting the polymer syringe with one end of the capillary column through a passage; and
   a high voltage power supply device having electrodes provided on the one end and the other end of the capillary column so that the electrode provided on the one end comes into contact with the polymer, for applying an electrophoresis voltage between the both ends of the capillary column with the electrodes.

2. The capillary electrophoretic apparatus in accordance with claim 1, wherein
   the pump block comprises a polymer port connected with the polymer syringe, a column port connected with the one end of the capillary column and a passage connecting the polymer port and the column port with each other, and
   the electrode on the one end is provided to come into contact with the polymer in the polymer syringe or the pump block.

3. The capillary electrophoretic apparatus in accordance with claim 1, further comprising a buffer syringe charged with a buffer, wherein
   the pump block comprises a polymer port connected with the polymer syringe, a buffer port connected with the buffer syringe, a column port connected with the one end of the capillary column and a passage connecting the ports with each other, and
   the electrode on the one end is provided to come into contact with the polymer through the buffer.

4. The capillary electrophoretic apparatus in accordance with claim 1, wherein
   the pump block comprises an openable drain port connected to the passage.

5. The capillary electrophoretic apparatus in accordance with claim 1, wherein
   the pump block comprises a pressure sensor measuring the pressure in the passage.

6. The capillary electrophoretic apparatus in accordance with claim 1, further comprising a tray storing a sample, a buffer and purified water,
   the tray being movable for inserting the other end of the capillary column and the electrode on the other end into the sample, the buffer or the purified water.

* * * * *

UNITED STATES PATENT AND TRADEMARK OFFICE
CERTIFICATE OF CORRECTION

PATENT NO.    : 6,383,356 B1
DATED         : May 7, 2002
INVENTOR(S)   : Hayashizaki et al.

It is certified that error appears in the above-identified patent and that said Letters Patent is hereby corrected as shown below:

<u>Title page,</u>
Item [73], Assignees should read:
-- [73] Assignees: The Institute of Physical and Chemical Research, Saitama; Shimadzu Corporation, Kyoto; Japan Science and Technology Corporation, Saitama, all of (JP) --

Signed and Sealed this

Fifteenth Day of October, 2002

*Attest:*

JAMES E. ROGAN
*Director of the United States Patent and Trademark Office*

*Attesting Officer*